United States Patent [19]

Geiger

[11] 4,074,715
[45] Feb. 21, 1978

[54] SYRINGE PLUNGER
[75] Inventor: Kenneth E. Geiger, Palisades Park, N.J.
[73] Assignee: Becton, Dickinson and Company, Rutherford, N.J.
[21] Appl. No.: 737,525
[22] Filed: Nov. 1, 1976
[51] Int. Cl.² ............................................. A61M 5/00
[52] U.S. Cl. ................................................ 128/218 P
[58] Field of Search ......... 128/218 P, 218 PA, 218 R, 128/218 C, 234, 2 F, 215

[56] References Cited
U.S. PATENT DOCUMENTS

| 1,139,368 | 5/1915 | Pierce | 128/218 P |
| 2,574,964 | 11/1951 | Eisenstark | 128/218 P |
| 3,045,674 | 7/1962 | Goldberg | 128/218 P |
| 3,890,956 | 6/1975 | Moorehead | 128/2 F |

FOREIGN PATENT DOCUMENTS

| 228,677 | 6/1960 | Australia | 128/218 P |
| 298,292 | 10/1928 | United Kingdom | 128/218 P |

Primary Examiner—John D. Yasko
Attorney, Agent, or Firm—Kane, Dalsimer, Kane, Sullivan and Kurucz

[57] ABSTRACT

The disclosure is of a novel syringe plunger characterized by a completely immobile piston head. The plunger is advantageously used in syringe assemblies and facilitates the so-called "micrometer" injection.

6 Claims, 10 Drawing Figures

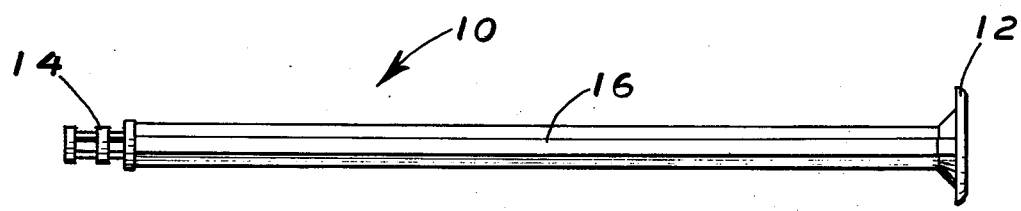
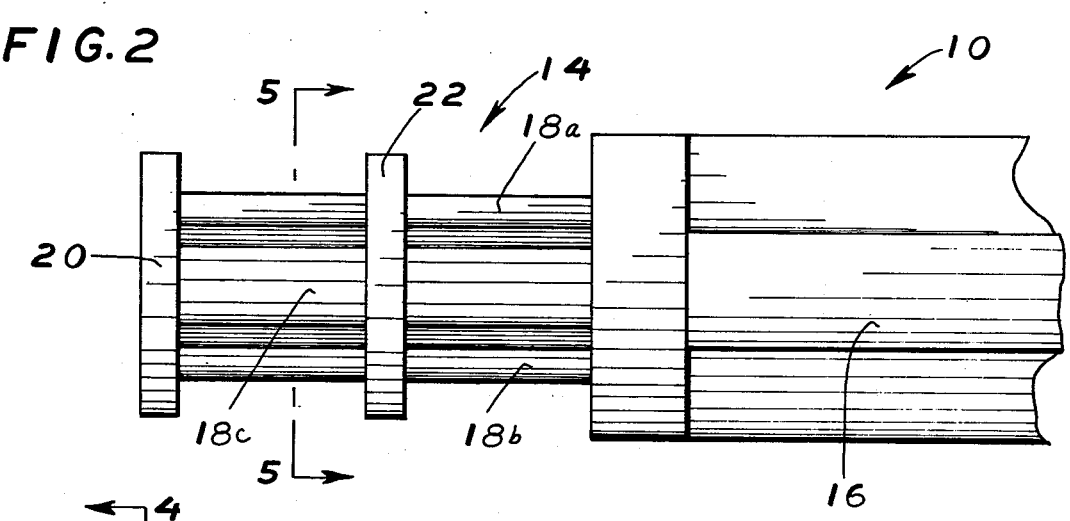
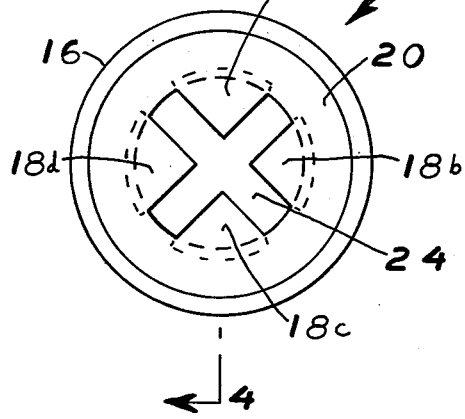
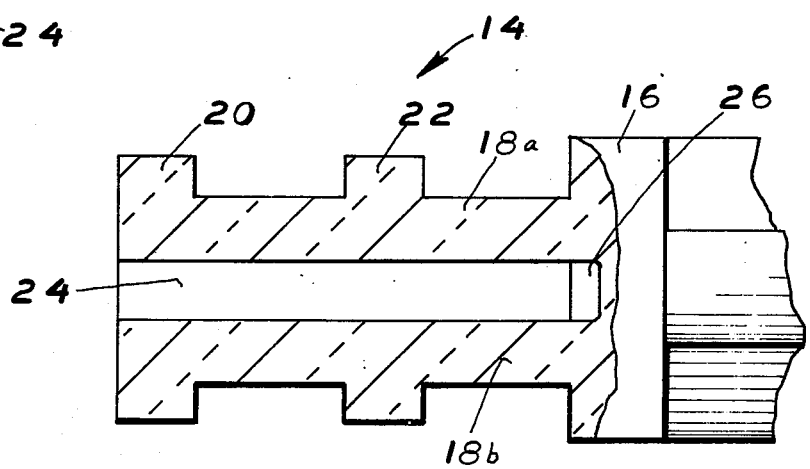

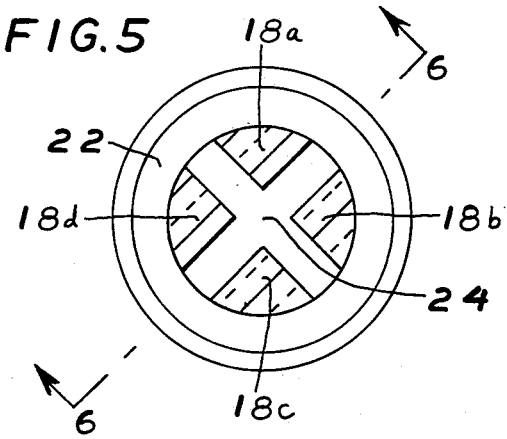
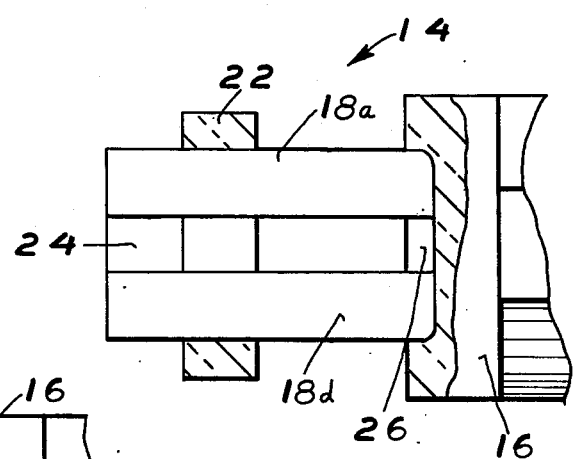
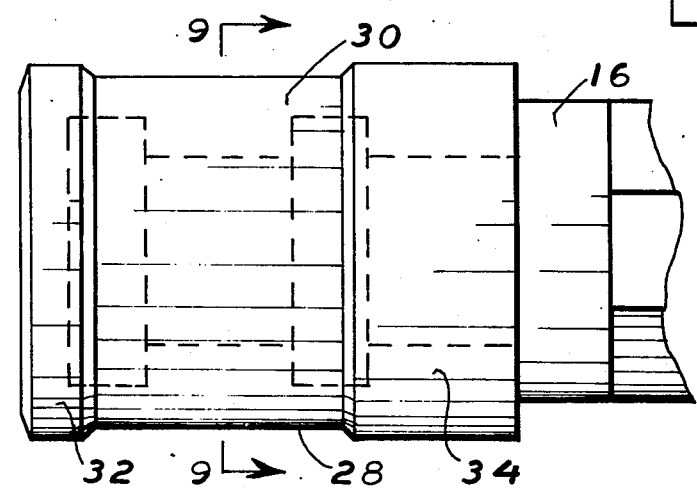
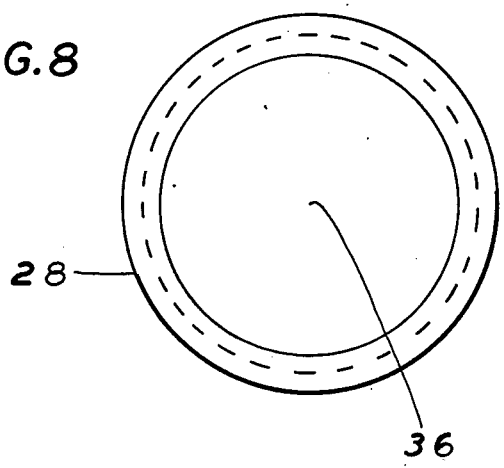
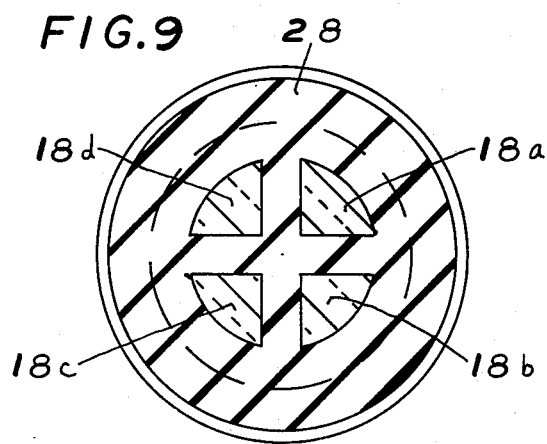

SYRINGE PLUNGER

BACKGROUND OF THE INVENTION

1. Field of the Invention

The invention relates to medical syringes and more particularly relates to the plunger component of medical syringes.

2. Brief Description of the Prior Art

Representative of the prior art are U.S. Pat. Nos. 2,695,612; 2,831,483; 2,886,034; 2,902,034; 3,016,896; 3,237,815; 3,581,956; and 3,656,480.

In general, syringe plungers of the prior art have not been entirely satisfactory for all purposes in that the piston head component has been mounted on the plunger shank in such a manner that when held in the confines of the syringe barrel, it may not be rotatable. It is advantageous to be able to rotate the piston-head within the confines of the syringe barrel, since this permits one to employ the syringe in the so-called "micrometer injection technique". This technique entails rotating the plunger, including the piston-head in the syringe barrel while gently pressing the plunger inwardly. This permits the operator to move the plunger micro distances in the barrel. It is the ultimate in control of injection volumes and rates.

The plunger of the invention is rotatable, including the piston-head. In addition the plunger of the invention is advantageous in that it requires fewer steps to assemble and is more economical to produce than prior art plungers.

SUMMARY OF THE INVENTION

The invention comprises a plunger for a syringe assembly, which comprises; a handle; a piston interlock; a shank joining said handle to the piston interlock; and a piston, immovably mounted on said interlock.

The term "piston interlock" as used throughout the specification and claims means a structure which will interengage with the body of the piston-head of a plunger in such a manner as to become permanently locked with the piston, immobilizing movement of the piston in any direction with respect to the rest of the plunger and being removable from engagement with the piston-head only by destruction of the piston-head and/or interlock means.

BRIEF DESCRIPTION OF THE DRAWINGS

FIG. 1 is an isometric view of an embodiment plunger of the invention without the piston-head component.

FIG. 2 is an enlarged view of the end of the plunger shank distal to the handle.

FIG. 3 is an end view of the end of the plunger shown in FIG. 2.

FIG. 4 is a cross-sectional view along lines 4—4 of FIG. 3.

FIG. 5 is a cross-sectional view along lines 5—5 of FIG. 2.

FIG. 6 is a cross-sectional view along lines 6—6 of FIG. 5.

FIG. 7 is a view as in FIG. 2 but with the piston-head mounted on the end.

FIG. 8 is an end view of the end shown in FIG. 7.

FIG. 9 is a cross-sectional view along lines 9—9 of FIg. 7.

DETAILED DESCRIPTION OF THE PREFERRED EMBODIMENTS OF THE INVENTION

Figure 10:
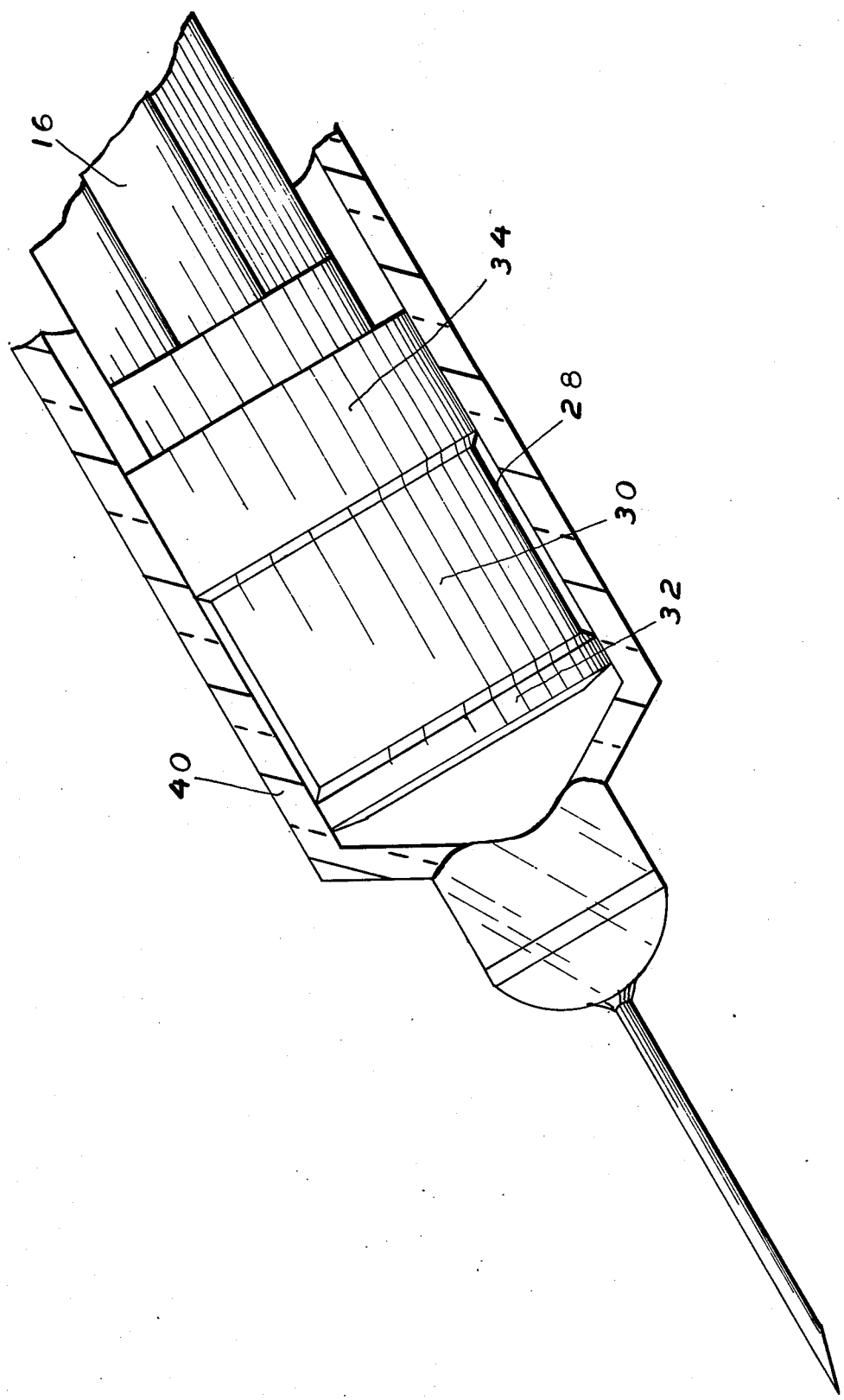
FIG. 10 is a cross-sectional-in-part view of a syringe showing the plunger end of FIG. 7 mounted therein.

With reference to the accompanying drawings of FIGS. 1-10, a preferred embodiment plunger 10 of the invention may be observed. As seen in FIG. 1, the plunger 10 has a handle 12 at one end and an interlock 14 at a second end of a shank 16 joining the two ends. FIG. 2 is an exploded view of the interlock 14 and shows it is an integrally molded extension of shank 16, comprising a plurality of bar extensions 18a, 18b, 18c, 18d joined together by rings 20, 22. The bars 18 have a triangular cross-section and are separated by space 24. Details of the interlock 14 structure may be further seen in the end view of ring 20 seen in FIG. 3 and in the FIG. 4, a cross-sectional view along lines 4—4 of FIG. 3. As seen in the FIG. 4, space 24 extends a short distance into shank 16 at zone 26. The spatial arrangement of the bars 18a, 18b, 18c and 18d may be seen by referring to the FIGS. 5 (a cross-sectional view along lines 5—5 of FIG. 2) and 6 (a cross-sectional view along lines 6—6 of FIG. 5).

The interlock 14 is designed to join a piston-head to shank 16 in such a manner that the piston-head is immovable in relation to the shank 16. That is, the piston-head will neither rotate on shank 16 or move off the shank 16. The shank 16 and interlock 14 are preferably of unitary construction and may be, for example, an integrally molded unit fabricated from a rigid polymeric resin such as a rigid polyethylene, polypropylene, polycarbonate, polyurethane, polyacrylic or like resins. FIG. 7 is a view as in FIG. 2 but with an elastomeric piston-head 28 mounted on the interlock 14. The piston head 28 may be fabricated from any elastomeric material and preferably comprises a central body portion 30 having expanded (in diameter) ends 32, 34. The expanded ends 32, 34 form sealing flanges to mate with the interior walls of a syringe barrel and to form a sliding seal therewith. FIG. 8 is an end view of piston 28 and shows the piston face 36. The attachment of piston 28 to shank 16 by interlock 14 may be seen in the FIG. 9, a cross-sectional view along lines 9—9 of FIg. 7. As shown, the space 24 (see FIG. 3) has been invaded and filled with the body of piston 28 so that the bars 18a, 18b, 18c, 18d and supporting rings 20, 22 are enmeshed and enclosed by the body of piston 28. In this manner, the piston 28 is immobilized on interlock 14 in such a way that it is impossible to rotate on the interlock 14 nor can it be pulled off the end of interlock 14 in either direction. The only way to remove the piston 28 from the interlock 14 is by a physical destruction of the interlock 14 and/or the piston 28.

The piston 28 may be formed in-situ on the interlock 14 by molding the elastomeric piston on the interlock 14. For example, employing an appropriate mold, a preformed shank 16 with handle 12 and interlock 14 may have injection molded thereon the elastomeric piston 28, using conventional techniques and apparatus. Any elastomeric material conventionally used as a piston head on syringes may be employed, for example polyurethane elastomers, polybutadiene rubbers and the like. Preferred as the elastomeric piston head 28 in the plungers of the invention is one fabricated from styrene-butadiene copolymer elastomers (Kraton G-2705, Shell Chemical Co.). Most preferred is an elastomeric piston head 28 fabricated from Kraton G-2705 containing as a filler a slip agent such as an organic fatty amide (Adogen 58, Ashland Chemical Corp.). The filler, present within the range of from about 0.01 to 1.0% by weight of the elastomer, provides a self lubricating piston-head 28. This preferred embodiment requires 50% less silicone type lubricant during assembly of the plunger in a medical syringe barrel 40 as shown in FIG. 10. The plunger 10 may be rotated within the barrel 40 in either direction. The piston-head 28 will rotate with shank 16, following the movement of shank 16 so that the piston-head 28 will freely rotate in the barrel 40. While rotating, the plunger 10 may be withdrawn or pushed in minute distances and the piston-head will respond the same distance as the shank 16. In this manner, the highest degree of control may be obtained over movement of the piston-head 28.

I claim:

1. A plunger for a syringe assembly, which comprises;
   a handle;
   a piston interlock;
   a shank joining said handle to the piston interlock;
   said interlock including a bar extending distally from said shank; and
   a piston, completely enmeshing and enclosing said bar and making full contact with the interlock, whereby said piston is immovably mounted on said interlock.

2. A plunger of claim 1 wherein said piston interlock is an integrally molded part of said shank.

3. A plunger of claim 1 wherein said interlock comprises a plurality of bars extending distally from said shank, said bars being joined together by a ring and spaced apart by intervening space, said piston completely enmeshing and enclosing said interlock and making full contact with the interlock, whereby said piston is immovably mounted on said interlock.

4. A plunger of claim 1 wherein said shank, handle and interlock are fabricated from a rigid polymeric resin and said piston is fabricated from a styrene-butadiene copolymer.

5. A plunger according to claim 4 wherein said copolymer is filled with a slip-agent.

6. A syringe assembly, which comprises;
   a syringe barrel;
   a plunger slidably mounted in said barrel, said plunger comprising;
   a handle;
   a piston interlock;
   a shank joining said handle to the piston interlock;
   said interlock comprising a plurality of bars extending distally from said shank, said bars being joined together by a ring and spaced apart by intervening space; and
   a piston, completely enmeshing and enclosing said interlock and making full contact with the interlock, whereby said piston is immovably mounted on said interlock and adapted to form a sliding seal with the inside walls of said barrel.

* * * * *